(12) United States Patent
D'Amico

(10) Patent No.: US 7,153,865 B2
(45) Date of Patent: Dec. 26, 2006

(54) N-TYPE CALCIUM CHANNEL ANTAGONISTS FOR THE TREATMENT OF PAIN

(75) Inventor: Derin D'Amico, Newbury Park, CA (US)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 10/488,025

(22) PCT Filed: Aug. 23, 2002

(86) PCT No.: PCT/SE02/01521

§ 371 (c)(1),
(2), (4) Date: Jan. 18, 2005

(87) PCT Pub. No.: WO03/018561

PCT Pub. Date: Mar. 6, 2003

(65) Prior Publication Data

US 2005/0131020 A1    Jun. 16, 2005

(30) Foreign Application Priority Data

Aug. 27, 2001    (SE) .................................... 0102858

(51) Int. Cl.
*A61K 31/47*    (2006.01)
*C07D 215/38*    (2006.01)
(52) U.S. Cl. ..................... 514/313; 546/161
(58) Field of Classification Search ............... 514/313; 546/161
See application file for complete search history.

(56) References Cited

U.S. PATENT DOCUMENTS 4,357,333 A * 11/1982 Archibald et al. .......... 514/313

FOREIGN PATENT DOCUMENTS

WO    WO 0064877 A1    11/2000

OTHER PUBLICATIONS

E.B. Pedersen, "Synthesis of 2,4-bis(dimethylamino)quinolines by hmpt induced ring closure of anthranilates," Tetrahedron Letters, p. 217-220, (Feb. 23, 1977).
Jorgen A. Jensen et al., "New One-step Synthesis of 2,4-bis(dialkylamino)quinoines and 4,6-bis(dialkylamino)thieno[2,3-b]pyridines," Chemica Scripta, vol. 28 (No. 4), p. 435-437, (Feb. 23, 1988).

* cited by examiner

*Primary Examiner*—D. Margaret Seaman
(74) *Attorney, Agent, or Firm*—Kenneth F. Mitchell; Cozen O'Connor, P.C.

(57) ABSTRACT

Compounds useful for the treatment of pain in accord with the following structural diagram,

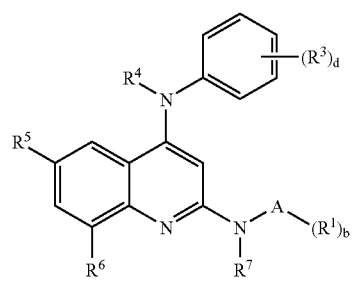

wherein A, $R^1$, b, $R^3$, d, $R^4$, $R^5$, $R^6$ and $R^7$ are any of a number of groups as defined in the specification, and pharmaceutical compositions and methods of treatment utilizing such compounds.

8 Claims, No Drawings

N-TYPE CALCIUM CHANNEL ANTAGONISTS FOR THE TREATMENT OF PAIN

This is a 371 of International Application No. PCT/SE02/01521, filed Aug. 23, 2002, which claims the benefit of Application No. 0102858-8 filed in Sweden on Aug. 27, 2001.

FIELD OF THE INVENTION

This invention relates to substituted quinoline compounds, methods of making such compounds and methods of using such compounds for the treatment or prevention of pain or nociception.

RELATED ART

Pain causes a great deal of suffering and is a sensory experience distinct from sensations of touch, pressure, heat and cold. It is often described by sufferers by such terms as bright, dull, aching, pricking, cutting or burning and is generally considered to include both the original sensation and the reaction to that sensation. This range of sensations, as well as the variation in perception of pain by different individuals, renders a precise definition of pain difficult. Where pain is "caused" by the stimulation of nociceptive receptors and transmitted over intact neural pathways, this is termed nociceptive pain. Pain may also be caused by damage to neural structures, and pain is often is manifested as neural supersensitivity; this type of pain is referred to as neuropathic pain.

The level of stimulation at which pain is perceived is referred to as the "pain threshold". Where the pain threshold is raised, for instance, by the administration of an analgesic drug, a greater intensity or more prolonged stimulus is required before pain is experienced. Analgesics are a class of pharmaceutical agent which, following administration to a patient in need of such treatment, relieve pain without loss of consciousness. This is in contrast to other pain-relieving drugs, for example, general anesthetics which obtund pain by producing a hiatus in consciousness, or local anesthetics which block transmission in peripheral nerve fibers thereby preventing pain.

Tachykinin antagonists have been reported to induce antinociception in animals, which is believed to be analogous to analgesia in man (for review see Maggi et al, J. Auton. Pharmacol. 13:23–93 (1993)). In particular, non-peptide NK-1 receptor antagonists have been shown to produce such analgesia, thus, for example, in classical tests of chemo-nociception (phenylbenzoquinone-induced writhing and formalin test) the NK-1 receptor antagonist RP 67,580 produced analgesia with potency comparable to that of morphine (Garret et al, Proc. Natl. Acad. Sci. USA 88:10208–10212 (1993)).

Opioid analgesics are a well-established class of analgesic agents. These compounds are generally accepted to include, in a generic sense, all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine).

Whilst an opioid partial agonist such as nalorphine, (the N-alkyl analogue of morphine) will antagonize the analgesic effects of morphine, when given alone it can be a potent analgesic in its own right. Of all of the opioid analgesics, morphine remains the most widely used and is a suitable archetype compound. Unfortunately, apart from its useful therapeutic properties, morphine also has a number of drawbacks including respiratory depression, decreased gastrointestinal motility (resulting in constipation) and, in some individuals, nausea and vomiting may occur. Another characteristic is the development of tolerance and physical dependence which may limit the clinical use of such compounds.

Anti-inflammatory compounds directed at blocking or reducing synovial inflammation, and thereby improving function, and analgesics directed to reducing pain, are presently the primary method of treating the rheumatoid diseases and arthritis. Aspirin and other salicylate compounds are frequently used in treatment to interrupt amplification of the inflammatory process and temporarily relieve the pain. Other drug compounds used for these purposes include phenylpropionic acid derivatives such as Ibuprofen and Naproxin, Sulindac, phenyl butazone, corticosteroids, antimalarials such as chloroquine and hydroxychloroquine sulfate, and fenemates. For a thorough review of various drugs utilized in treating rheumatic diseases, reference is made to J. Hosp. Pharm., 36:622 (May 1979).

Calcium channels are membrane-spanning, multi-subunit proteins that allow controlled entry of $Ca^{++}$ ions into cells from the extracellular fluid. Such channels are found throughout the animal kingdom, and have been identified in bacterial, fungal and plant cells. Commonly, calcium channels are voltage dependent. In such channels, the "opening" allows an initial influx of $Ca^{++}$ ions into the cells which lowers the potential difference between the inside of the cell bearing the channel and the extracellular medium bathing the cell. The rate of influx of $Ca^{++}$ ions into the cell depends on this potential difference. All "excitable" cells in animals, such as neurons of the central nervous system ("CNS"), peripheral nerve cells, and muscle cells, including those of skeletal muscles, cardiac muscles, and venous and arterial smooth muscles, have voltage-dependent calcium channels. Calcium channels are physiologically important because the channels have a central role in regulating intracellular $Ca^{++}$ ions levels. These levels are important for cell viability and function. Thus, intracellular $Ca^{++}$ ion concentrations are implicated in a number of vital processes in animals, such as neurotransmitter release, muscle contraction, pacemaker activity, and secretion of hormones.

It is believed that calcium channels are relevant in certain disease states. A number of compounds useful in treating various cardiovascular diseases in animals, including humans, are thought to exert their beneficial effects by modulating functions of voltage-dependent calcium channels present in cardiac and/or vascular smooth muscle. Many of these compounds bind to calcium channels and block, or reduce the rate of, influx of $Ca^{++}$ ions into the cells in response to depolarization of the cell membrane. An understanding of the pharmacology of compounds that interact with calcium channels in other organ systems, such as the central nervous system, and the ability to rationally design compounds that will interact with these specific subtypes of human calcium channels to have desired therapeutic, e.g., treatment of neurodegenerative disorders, effects have been hampered by an inability to independently determine how many different types of calcium channels exist or the molecular nature of individual subtypes, particularly in the CNS, and the unavailability of pure preparations of specific channel subtypes, i.e., systems to evaluate the specificity of calcium channel-effecting compounds.

Multiple types of calcium channels have been detected based on electrophysiological and pharmacological studies of various mammalian cells from various tissues (e.g., skeletal muscle, cardiac muscle, lung, smooth muscle and brain) Bean, B. P., Annu. Rev. Physiol. 51:367–384 (1989) and Hess, P., Annu. Rev. Neurosci. 56:337 (1990). These different types of calcium channels have been broadly categorized into four classes, L-, T-, N-, and P-type, distinguished by current kinetics, holding potential sensitivity and sensitivity to calcium channel agonists and antagonists. Four subtypes of neuronal voltage-dependent calcium channels have been proposed Swandulla, D. et al, Trends Neurosci 14:46 (1991). The L-, N-, and P-type channels have each been implicated in nociception, but only the N-type channel has been consistently implicated in acute, persistent and neuropathic pain. A synthetic version of ω-conotoxin MVIIA, a 25-amino acid peptide derived from the venom of the piscivorous marine snail, Conus magus has been used intrathecally in humans and has ~85% success rate for the treatment of pain with a greater potency than morphine.

While known drug therapies have utility, there are drawbacks to their use. For instance, it may take up to six months of consistent use of some medications in order for the product to have effect in relieving the patient's pain. Consequently, a particular subject may be receiving treatment and continuing to suffer for up to six months before the physician can assess whether the treatment is effective. Many existing drugs also have substantial adverse side effects in certain patients, and subjects must therefore be carefully monitored. Additionally, most existing drugs bring only temporary relief to sufferers and must be taken consistently on a daily or weekly basis for continued relief. Finally, with disease progression, the amount of medication needed to alleviate the pain may increase thus increasing the potential for side effects. Thus, there is still a need for an effective and safe treatment to alleviate pain.

SUMMARY OF THE INVENTION

In one aspect the present invention provides compounds having selective action at N-type calcium channels that are useful for the treatment of pain.

Compounds of the present invention that show selective action at N-type calcium channels are compounds in accord with structural diagram I,

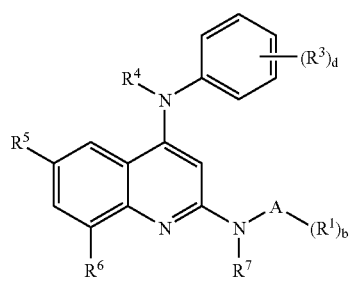

I wherein:

A is selected from phenyl, heteroaryl or bicyclic heteroaryl;

$R^1$ at each occurrence is independently selected from halogen, $(C_1-C_6)$alkyl, heterocyclyl, OH, $(C_1-C_6)$alkoxy, or $NR^2_2$;

b is an integer selected from 0, 1, 2 or 3;

$R^2$ at each occurrence is independently selected from H or $(C_1-C_4)$alkyl;

$R^3$ at each occurrence is independently selected from halogen or $(C_1-C_4)$alkyl;

d is an integer selected from 0, 1, 2 or 3;

$R^4$ is selected from H or $(C_1-C_4)$alkyl;

$R^5$ is selected from the group consisting of H, halogen, $(C_1-C_3)$alkyl, $(C_1-C_3)$perfluoroalkyl, $(C_1-C_3)$alkoxy, hydroxy, $NH_2$ or $NHR^2$;

$R^6$ is selected from the group consisting of H, halogen, $(C_1-C_6)$alkyl, $(C_1-C_4)$perfluoroalkyl, $(C_1-C_6)$alkoxy, hydroxy, $(C_1-C_6)$alkanoyl, $C(=O)NR^2_2$ or $NR^2_2$; and $R^7$ is selected from H or methyl.

Particular compounds of the present invention are those in accord with structural diagram I wherein;

A is selected from phenyl or bicyclic heteroaryl;

$R^1$ at each occurrence is independently selected from halogen, $(C_1-C_6)$alkyl, heterocyclyl, OH, $(C_1-C_6)$alkoxy, or $NR^2_2$;

b is an integer selected from 0, 1, 2 or 3;

$R^2$ at each occurrence is independently selected from H or $(C_1-C_4)$alkyl;

$R^3$ at each occurrence is independently selected from halogen or $(C_1-C_4)$alkyl;

d is an integer selected from 0, 1, 2 or 3;

$R^4$ is H;

$R^5$ is selected from H, halogen, $(C_1-C_3)$alkyl, $(C_1-C_3)$perfluoroalkyl or $(C_1-C_3)$alkoxy;

$R^6$ is selected from H, halogen, $(C_1-C_6)$alkyl, $(C_1-C_4)$perfluoroalkyl, $(C_1-C_6)$alkoxy, hydroxy, $(C_1-C_6)$alkanoyl, $C(=O)NR_2$ or $—NR^2$; and $R^7$ is H.

Most particular compounds of the invention are those exemplified herein.

In another aspect, the invention comprises a method for using compounds according to structural diagram I for the treatment of pain, said method comprising administering a pain-ameliorating effective amount of any such compound.

One embodiment of the method of the invention comprises administering a pain-ameliorating effective amount of a compound in accordance with structural diagram I to a subject in need of treatment for acute, persistent or neuropathic pain.

In a further aspect, the invention comprises methods for making compounds in accord with structural diagram I.

In yet another aspect, the invention comprises pharmaceutical compositions comprising compounds in accord with structural diagram I together with excipients, diluents or stabilizers, as further disclosed herein, useful for the treatment of acute, persistent and neuropathic pain.

DETAILED DESCRIPTION OF THE INVENTION

Compounds of the invention are those within the scope of the generic description and particularly those compounds exemplified hereafter.

Suitable pharmaceutically-acceptable salts of compounds of the invention include acid addition salts such as methanesulfonate, fumarate, hydrochloride, hydrobromide, citrate, tris(hydroxymethyl)aminomethane, maleate and salts formed with phosphoric and sulfuric acid.

Where compounds of the present invention possess a chiral center it is to be understood that the invention encompasses all optical isomers and diastereoisomers of such compounds.

Where compounds of the present invention can tautomerize it is to be understood that the invention encompasses all tautomeric forms of such compounds.

Where compounds of the present invention can exist in unsolvated as well as solvated forms such as, for example, hydrated forms, it is to be understood that the invention encompasses all such solvated and unsolvated forms.

Another aspect of the invention provides processes for making compounds of the invention. Generally compounds of the present invention were prepared by reacting in an automated fashion substituted 2-chloro-4-aminoquinoline intermediates with aminoaryl precursors. The intermediate substituted 2-chloro-4-aminoquinolines were prepared by chlorination of substituted 2-hydroxy-4-aminoquinoline precursors, which were in turn prepared by amination of substituted 2,4-quinolinediol precursors.

a) 2-Hydroxy-4-aminoquinoline precursors in accord with structural diagram III were prepared by reacting a substituted 2,4-quinolinediol in accord with structural diagram II with three equivalents of an aryl amine in N-methylpyrrolidinone and 6N HCL in 2-propanol, in a sealed tube at a temperature of about 180° C.

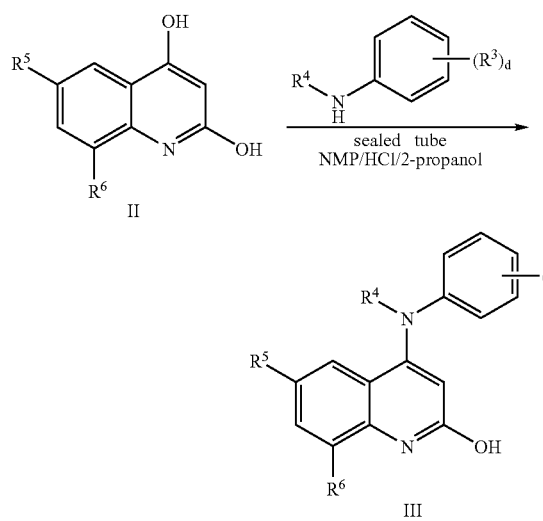

wherein $R^3$, $R^4$, $R^5$, $R^6$ and d, are as heretofore defined;

a') 2-hydroxy-4-aminoquinoline precursors in accord with structural diagram III were alternatively prepared by reacting a substituted 2,4-quinolinediol in accord with structural diagram II with two equivalents of an aryl amine in N-methylpyrrolidinone and 4N HCL in dioxane, in a sealed teflon tube. The reaction was maintained at a temperature of about 200° C. using an Ethos 1600 Lab Microwave as the energy source.

b) 2-chloro-4-aminoquinoline precursors were prepared by chlorinating a 2-hydroxy-4-aminoquinoline compound in accord with structural diagram III by refluxing with POCl$_3$ to form a compound according to structural diagram IV.

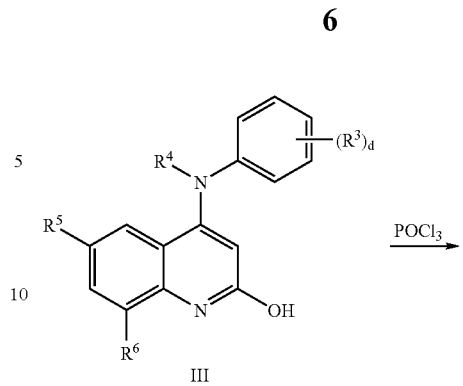

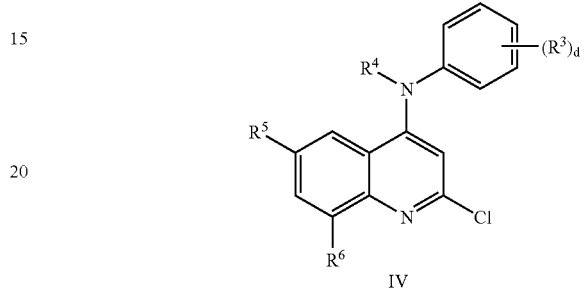

wherein $R^3$, $R^4$, $R^5$, $R^6$, b and d are as heretofore defined;

c) Compounds of the present invention in accord with structural diagram I were prepared by reacting 2-chloro-4-aminoquinoline precursors with aromatic amines in N-methylpyrrolidinone at temperatures of 100–180° C.

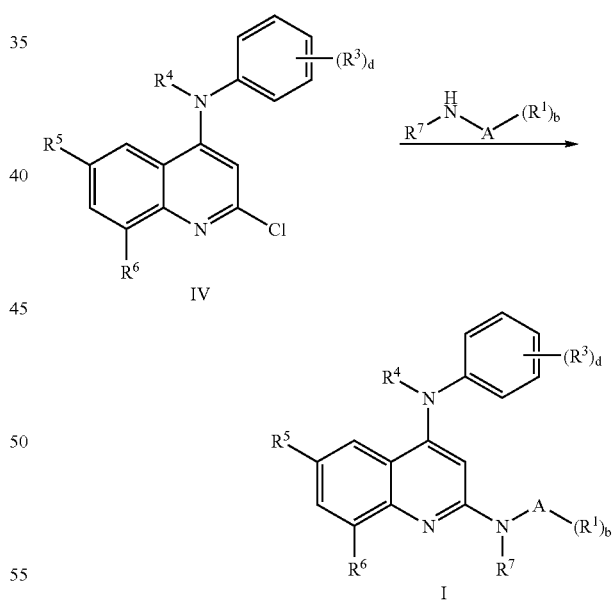

wherein $R^1$, $R^3$, $R^4$, $R^5$, $R^6$, $R^7$, b and d are as heretofore defined.

The procedure of step c) may also be performed in a parallel fashion using a robotic instrumentality. A suitable robotic instrumentality for such a multiple parallel synthesis is a ChemSpeed robot.

To use a compound of the invention or a pharmaceutically-acceptable salt thereof for the therapeutic treatment or prophylactic treatment of pain in mammals, which may be humans, the compound can be formulated in accordance with standard pharmaceutical practice as a pharmaceutical composition. Accordingly, a further aspect of the invention provides a pharmaceutical composition which contains a compound of the structural diagram I as defined herein or a pharmaceutically-acceptable salt thereof, in association with at least one pharmaceutically-acceptable additive such as an excipient or carrier.

In methods of the invention, treatment is contemplated to be administered in any physiologically-acceptable, such as by topical application, ingestion, inhalation insufflation or injection. Topical application, for example may be by a dermal, sublingual, nasal, vaginal or rectal route. Injection may be intradermal, subcutaneous, parenteral, intraperitoneal, intravenous, intramuscular or by infusion. Ingestion may be of a capsule a tablet, or a liquid. Suitable pharmaceutical compositions that contain a compound of the invention may be formulated by means known in the art in the form of, for example, tablets, capsules, aqueous or oily solutions or suspensions, emulsions, creams, ointments, gels, nasal sprays, suppositories, finely divided powders or aerosols for inhalation, and for injection sterile aqueous or oily solutions or suspensions or sterile emulsions. A preferred route of administration is orally by tablet or capsule.

In addition to a compound of the present invention, a pharmaceutical composition of this invention may also contain one or more other pharmacologically-active agents. Alternatively, a pharmaceutical composition comprising a compound of this invention may be co-administered simultaneously or sequentially with one or more other compatible pharmacologically-active agents.

Pharmaceutical compositions of this invention will normally be administered so that a pain-ameliorating effective daily dose is received by the subject. The daily dose may be given in divided doses as necessary, the precise amount of the compound received and the route of administration depending on the weight, age and sex of the patient being treated and on the particular disease condition being treated according to principles known in the art. A preferred dosage regime is once daily.

A yet further embodiment of the invention provide the use of a compound of the structural diagram I, or a pharmaceutically-acceptable salt thereof, in the manufacture of a medicament useful for binding to N-type calcium channels in a warm-blooded animal such as a human being.

Still another embodiment of the invention provides a method of binding a compound of the invention to N-type calcium channels of a warm-blooded animal, such as a human being, in need of treatment for pain, which method comprises administering to said animal an effective amount of a compound of structural diagram I or a pharmaceutically-acceptable salt thereof.

A further aspect of the present invention provides a pharmaceutical composition which includes a compound of the present invention as defined herein or a pharmaceutically-acceptable salt thereof, in association with a pharmaceutically-acceptable additive such as an excipient or a carrier.

A still further aspect of the present invention is a method of treatment of the human or animal body that includes the administration of a compound of the present invention or a pharmaceutically-acceptable salt thereof.

DEFINITIONS

When used herein "halo" or "halogen" means fluoro, chloro, bromo or iodo;

when substituents herein are stated to be "selected from" or "independently selected from" a group of moieties, it is to be understood that included compounds are those where all substituents are the same and compounds where each substituent may be different;

when used herein, the term heterocyclyl includes 5–7 membered rings containing 1, 2 or 3 heteroatoms selected from the group consisting of N, O and S and bicyclic rings containing such atoms and includes such groups as tetrahydrofuryl, dihydropyrrolynyl, tetrahydroisoquinolinyl, tetrahydrothiophene, oxiranyl, azidiridynl and oxetanyl when used herein, the term heteroaryl includes such groups as pyridinyl, pyrrole, thiophenyl and furanyl;

when used herein the term "alkyl," as in for example $(C_1-C_6)$alkyl, unless otherwise defined, includes both straight, branched and cyclic chain alkyl groups. References to individual alkyl groups such as "propyl" mean the normal, straight chain form, that is, n-propyl;

when used herein, a term such as "$(C_1-C_6)$alkyl" means alkyl groups having 1, 2, 3, 4, 5 or 6 carbon atoms and collective groups such as $(C_1-C_4)$alkyl and includes straight, branched and cyclic moieties, straight chain moieties include for example methyl, ethyl and propyl, branched chain moieties include for example iso-propyl and t-butyl, cyclic moieties include for example cyclopentyl and cyclopropylmethyl; similarly, a term such as "$(C_1-C_3)$alkoxy" includes particular moieties such as methoxy, ethoxy and propoxy, and terms used herein that are not otherwise defined are intended to have their conventionally-understood meaning.

The Methods and Examples which follow are intended to illustrate but not limit the invention. In the Methods and Examples, unless otherwise stated:

concentrations of solutions were carried out by rotary evaporation in vacuo;

operations were carried out at ambient temperature, that is in the range 18–26° C. and under a nitrogen atmosphere;

column chromatography (by the flash procedure) was performed on Merck Kieselgel silica (Art. 9385);

yields are given for illustrative purposes only and are not necessarily the maximum attainable;

the structure of compounds according to structural diagram I were generally confirmed by conventional NMR (Bruker Avance 300) and mass spectrometry techniques, peak multiplicities are shown thus: s, singlet; bs, broad singlet; d, doublet; AB or dd, doublet of doublets; t, triplet; dt, double of triplets; m, multiplet; bm, broad multiplet; FAB m/s data were obtained using a Platform spectrometer (supplied by Micromass) run in electrospray and, where appropriate, either positive ion data or negative ion data were collected, herein $(M+H)^+$ is quoted;

purity of intermediates were was in general assessed by LC/MS and/or NMR analysis; and where used the following abbreviations have meanings as follows:

| | |
|---|---|
| DCM | is dichloromethane, |
| DMF | is N,N-dimethylformamide, |
| DMSO | is dimethylsulfoxide, |
| $CDCl_3$ | is deuterated chloroform, |
| FAB | is fast atom bombardment, |
| LC/MS | is mass spectrometry linked to liquid chromatography instrumentation |
| m/s | is mass spectroscopy or mass spectral, |
| NMR | is Nuclear Magnetic Resonance, |
| NMP | is N-methylpyrrolidinone, |
| TFA | is trifluoroacetic acid, and |
| THF | is tetrahydrofuran. |

BIOLOGICAL METHODS

I. N-channel FLIPR (Fluorescent Laser Imaging Plate Reader) Assay

The methods described herein provide a reliable FLIPR-based readout of the efficacy and potency with which test compounds inhibit calcium flux through the N-type calcium channel expressed in its native form in a human-derived neuroblastoma cell line differentiated chemically to a neuronal phenotype. The degree to which a compound at a particular concentration inhibited the N-channel calcium flux was determined by comparing the amplitude of peak calcium increase in the presence of the compound to a control 80 mM $K^+$ stimulus in wells without compound. Results obtained for this FLIPR assay were validated in two ways:

a) the N-channel specific peptide toxin, conotoxin MVIIA, showed an $IC_{50}$=3 nM (determined from fit to five-point concentration response analysis), compatible with the known literature value; and b) $IC_{50}$ values were determined certain compounds of the invention ($IC_{50}$ range: 2.37–10.54).

Potency of these same test compounds as inhibitors of the N-type calcium current was also determined by direct electrophysiological measurement either in neuronally differentiated IMR-32 cells, or in freshly-isolated rat superior cervical ganglion neurons $pIC_{50}$'s yielded by the two methodologies for the compound set were closely comparable (r=0.91; p<0.001).

A. Cell Culture

An immortalized cell line, IMR32, derived from human neuroblastoma cells obtained from the ATCC (product #CCL-127) was used for all experiments. Cells were grown in T75 flasks containing Eagle's minimum essential medium (MEM) w/Earle's salts and non-essential amino acids without glutamine (Cat.#SLM-034-B, Specialty Media, Philipsburg, N.J.), 10% FBS and 1% glutamine. Cells were grown to ~70–80% confluency (by visual microscopic estimation) before sub-culturing. To maintain a stock culture, cultures were split at a ratio of 1:3–1:4 by creating a cell suspension by trituration, and pipetting a volume of the cell suspension sufficient to yield this final ratio into new flasks containing ~20 mL of fresh media. Sub-culturing was generally performed two times per week. For preparation of 96 well plates (black-walled; Cat # 3603, Costar Co., Cambridge, Mass.), a T75 flask containing cells of desired confluency was brought up to 120 mL volume with media. Cells were then freed by trituration, and the cell suspension was plated into 12–96 well plates to yield final well volume of 100 µL.

B. Cell Differentiation to Neuronal Phenotype

Cells were induced to differentiate in a differentiation medium consisting of: MEM, 10% FBS, 1% glutamine, 1 µM 2-butyl-cAMP(49.1 mg/100 mL media(Cat. # D-0627, Sigma Corp., St Louis, Mo.), and 2.5 nM bromo-deoxyuridine (stock: 30.7 mg/10 mL media, 25 mL of above stock/100 mL media; Sigma Cat .# B-9285). To induce differentiation, the cells were treated with differentiation media (by complete medium change) 2 days after an initial plating in 96 well plates. Confluency at this time was ~40%. A complete medium change with freshly prepared differentiating medium was subsequently performed every 2–3 days. Cells were exposed to these differentiation conditions for 6 to 11 days before being used in FLIPR experiments.

C. Standard Experimental Solutions

Solutions of the following composition (in nM) were used in experiments (Buffers without probenicid purchased from Specialty Media (Buffers A and B: Cat. # BSS053A; Buffers C & D: Cat. # BSS056A).

Buffer A (first wash buffer): Krebs-Ringer-HEPES (KRH) buffer: NaCl: 125, KCl: 5, $MgSO_4$: 1.2, $KH_2PO_4$: 1.2, $CaCl_2 2H_2O$: 2, Glucose: 6, HEPES: 25, pH: 7.4 (pH adjusted with NaOH).

Buffer B (dye loading buffer) KRH buffer with 2.5 µM probenicid: same as buffer A, but probenicid added to final concentration of 2.5 µM. Probenecid (Cat. # P-8761, Sigma Chemical Co., St. Louis, Mo.) made as a stock solution at 250 mM.

Buffer C (dye washout buffer) KRH buffer with 0 mM $K^+$ and 2.5 µM probenicid: NaCl: 130, $MgSO_4$:1.2, $NaH_2PO_4$: 1.2, $CaCl_2$ $2H_2O$: 2, Glucose: 6, HEPES: 25, pH: 7.4 (pH adjusted with NaOH).

Buffer D (compound dilution buffer). Buffer C with 0.1% w/v bovine serum albumin (BSA; Sigma).

D. Pharmacological Standards and Compounds

The following solutions were used to obtain the data disclosed herein.

Nitrendipine: (RBI Chemicals, Natick, Mass.): Stock: 10 mM in DMSO; Pipetting solution: 9 µM; pipette 20 µL into 120 µL volume in well for final well concentration: 1 µM.

w-Conotoxin MVIIA: (Cat. # H-8210; Bachem Inc., Torrance, Calif.): Stock: 1 mM in HPLC grade $H_2 0$ with 0.1% BSA; Pipetting solution: 4.5 µM; pipette 20 µl into 140 µl volume in well for final well concentration: 1 µM.

Test compound stock and solution preparation: Compounds prepared daily as stocks at 10 mM in 100% DMSO; Pipetting solution: 45 µM or serial dilutions thereof; pipette 20 µL into 140 µL volume in well for final well concentration: 1 µM or 10-fold dilutions thereof.

High potassium (depolarization) solution: Buffer C with 240 mM $K^+$ added; pipette 80 µL into 160 µL volume in well for final well concentration of 80 mM $K^+$.

E. Cell Loading with Fluorescent Dyes

Fluorescent dye solution preparation: A calcium indicator dye, Fluo-4 acetylmethylester (Fluo 4-AM; Cat. # F-124201; Molecular Probes, Eugene, Oreg.) was used to measure changes in intracellular free calcium with FLIPR. 1 mM Fluo-4 µM stock solution was made by dissolution in DMSO. This stock was then diluted to 4.6 µM with Buffer B (Fluo-4 AM working solution).

Cell loading procedure: Plates containing cells were washed with Buffer A using an automated cell washer (Model #: 5161552, Labsystems Oy, Helsinki, Finland) with controls set to the following parameters: cell height: C/D; cell pulse: 4/5, washes: 3; volume: 5; DRY position setting. These settings resulted in a 70 µL residual depth of buffer over cells in each well. 100 µL of the Fluo-4 AM working solution was then added to each well resulting in a final Fluo-4 AM concentration of 2.7 µM Cells were incubated in this solution at 37° C. for 1–1.5 h. Cells were then washed with Buffer C five times using the cell washer with parameters the same as the pre-loading washes above with the exceptions of: washes: 5; WET position setting. A final wash was then conducted by changing the parameters as follows: washes: 1; volume: 2. This resulted in a final well volume of 120 µL. Cells were allowed to equilibrate under this condition for 10 min, and then used in the FLIPR protocol.

F. FLIPR Protocol

Instrumentation: Real time changes in intracellular free calcium in response to potassium-induced depolarization in the absence or presence of putative N-channel inhibitors were measured by either a FLIPR I or FLIPR II (configured for 96-well format) instrument (Molecular Devices, Sunnyvale, Calif.). Identical settings and protocols were used with each instrument, and results obtained from the two instruments were indistinguishable for a set of standard benchmark compounds.

FLIPR hardware settings: Laser power was set to about 0.3 watts. Excitation wavelength was set to a 488 nm peak, and the emission wavelength to 540 nm. Camera aperture was set to 2. All experiments were conducted at room temperature (20–22° C.).

Plate layout—reference signals: Certain wells on each plate were allocated to standards to determine minimum and maximum specific fluorescent signal against which inhibitory effects of compounds were normalized. The reference standards were distributed at plate locations including edge and interior wells.

Maximum signal (N-channel+non-specific): 12 wells were incubated in nitrendipine (1 µM) solution and 80 mM $K^+$ added to determine maximal $Ca^{2+}$ increase mediated by N-channels+non-specific (non-L-, non-N-channel mediated fluorescence increase). The coefficient of variation amongst these wells for the $K^+$-evoked peak increase in fluorescence units was typically less than 12%.

Minimum signal (non-specific): 6 wells were incubated in nitrendipine (1 µM)+w-conotoxin MVIIA and 80 mM $K^+$ added to determine background $Ca^{2+}$ with all N-channels pharmacologically occluded The peak non-specific signal component was typically less than 15% of the maximum signal peak amplitude.

N-channel reference small molecule: A compound that had been characterized extensively with respect to N-channel inhibitory activity in both FLIPR and patch clamp electrophysiology was included on each plate in triplicate at 1 µM (near $IC_{50}$) to establish a reference point.

Test compounds: 5 test compounds were evaluated for potency on each plate. Each compound was tested at 5 increasing concentrations spanning half-log units and typically reaching a maximal concentration of 10 µM. Each concentration was tested in triplicate wells.

Protocol structure: The FLIPR protocol was configured as three solution addition/sampling sequences (see below). Conotoxin (1 µM final conc.) was added to appropriate wells prior to placing the plate in the FLIPR instrument. Wells initially contained a total solution volume of 100 µl, and after all three solution additions contained 240 µl. The active mixing (by the pipette) option was not used in any sequence.

Nitrendipine addition sequence: 28 s total duration with fluorescence signal sampling at 1 Hz for 2 s, followed by addition of 20 µL nitrendipine standard solution at 10 µL/s, followed by sampling at 0.5 Hz for 24 s.

Test compound addition sequence: 64 s total duration with sampling at 0.5 Hz for 4 sec, test solution addition of 40 µL at 20 µL/s, followed by sampling at 0.2 Hz for 60 s.

Compound incubation, cell depolarization and calcium readout sequence: 1024 s total duration with sampling at 0.0167 Hz for 840 s, followed by solution addition 80 µL of high $K^+$ (depolarization) solution, followed by sampling at 1 Hz for 180 sec. This final 180 sec sampling interval thus represented the epoch where the peak increase in intracellular calcium due to flux through activated N-channels occurred.

G. Data Analysis

FLIPR software: Prior to export, the data was normalized within the FLIPR software module for two effects.

Baseline correction: The baseline was corrected by "zeroing" at sample # 57 (immediately prior to KCl addition). This normalization served to correct the y axis offset of the fluorescent trace from each well so that all traces had a common point just prior to onset of the relevant evoked fluorescent increase.

Spatial uniformity correction factor: The data was normalized by a procedure which calculates a mean over the plate of fluorescent units from the first sample, and then multiplies the data from each well by a scalar that adjusts the value of the first sample to this average value, thus normalizing for differences in absolute baseline fluorescence amongst the wells caused by differences in cell densities or dye loading.

External software: Data were exported from FLIPR into Excel as "*.squ" extension files. Following export, operations were performed in Excel to calculate the maximal peak amplitude (relative to the zeroed baseline) of the fluorescence increase following potassium addition in each well. Measurements from wells where an test compound was added were then normalized as a percentage between the mean amplitudes from the reference wells providing the maximum (100%) and non-specific (0%) signal components, as described above. The resulting percent inhibition by test compounds was considered to reflect inhibition of calcium flux at the N-type channel.

II. Formalin Test

The Formalin test assesses the inhibitory effects of orally administered N-type calcium channel antagonists on formalin-induced nocifensive behaviours in rats. The formalin test is a well established pain test (Dubuisson and Dennis, 1977; Wheeler-Aceto et al., 1990; Coderre et al., 1993). This test consists of two distinct phases of formalin-induced behavior. The first phase response, occurring between 0 to 5 minutes, is caused by acute nociception to the noxious chemical (formalin) injected into the paw. This is followed by a quiescent period of between 5 to 15 min post injection. A second phase response, occurring after 15 minutes and lasting up to 60 minutes, is caused by sensitization of the central neurons in the dorsal horn. Central sensitization augments the noxious afferent input and a stronger pain barrage is transmitted into the brain. Inhibition of the second phase response is indicative of a central mechanism of drug action.

The procedure for the formalin test is as follows: male rats are placed in a Plexiglas chamber and observed for 30–45 min. to observe their baseline activity. Multiple groups of animals are pretreated with either vehicle or different doses of a test compound. Animals are dosed with the drug of interest either 40 min., if by the intraperitoneal route, or 90 min., if by the oral route, prior to injection of formalin into a hind paw (under the dorsal skin; 0.05 mL of sterile 5% formalin). The number of paw flinches and licks during first phase (0–5 min.) and second phase (20–35 min.) are scored and recorded. Flinch and lick responses are calculated as percentage of inhibition compared with the mean score of a saline control group. Drug potencies are expressed as the dose which causes 50% of the maximum inhibitory effect, ("$ID_{50}$"). Student t-tests are used for statistical analysis to determine the significance of drug effects. Compounds are considered active based on their ability to inhibit the flinch response.

CHEMICAL METHODS 2-hydroxyquinoline and 2-chloroquinoline intermediates of exemplary compounds disclosed herein, see Table 1, were prepared as described below.

Starting quinoline diols were made using a standard procedure (Fischer, M., R. Laschober, et al. (1996). "3,4,8-Trimethoxy-2-quinolone. Synthesis of a new alkaloid from Eriostemon gardneri." Sci. Pharm. 64(3/4): 353–358; Patel, G. H. and C. M. Mehta (1960). "Synthesis of 2,4-Dihydroxyquinolines Using Polyphosphoric Acid as the Cyclizing Agent." J. Sci. Industrial Res. 19B: 436). The methods and subject matter of these journal articles are incorporated herein in their entirety by reference. All other reagents were purchased from Acros organics and used directly.

Intermediate 1

6-methoxy-4-(3,4-dichlorophenyl)amino-2-hydroxyquinoline

General procedure 1

6-Methoxyquinolinediol (2.5 g, 13.08 mmol) and 3,4-dichloroaniline (4.2 g, 26.25 mmol) were placed in a 100 mL Teflon vessel for use with an Ethos 1600 Lab Microwave. NMP was then added (9 mL), followed by HCl in dioxane (5 mL, 4 M). The slurry was irradiated to achieve a 200° C. temperature using a 400 W upper setpoint for 30 min. The mixture was cooled, suspended in methanol (20 mL), and filtered to afford 1.049 g of the title compound. $^1$H NMR (300 MHz, DMSO): 3.84 (s, 3H), 5.84 (s, 1H), 7.23 (td, ?H, J=8.88, 8.48 Hz), 7.35(tt, ?H, J=8.88, 2.42 Hz), 7.56(d, ?H, J=2.42 Hz), 7.66 (~s, 2H), 8.71(s, 1H), 11.10(s, 1H).

Intermediate 2

4-(3,4-dichlorophenyl)amino-2-hydroxyquinoline

General procedure 2

2,4-quinolinediol (10.0 g, 62.1 mmol) and 3,4-dichloroaniline (13.1 g, 80.7 mmol) were heated to 190° C. in 25 mL NMP for 48 h. After heating was discontinued, solids began to precipitate. These were collected, treated with 8.5 mL of HCl in isopropanol and sonicated in a 4:1 mixture of acetone:isopropanol. After 2.5 h of sonication, the solids were collected. The sonication cycle was repeated to afford 6.79 g of material (19.9 mmol, 32%). $^1$H NMR (300 MHz, DMSO): 12.7 (s,1 H), 9.34 (s, 1 H), 8.41 (d, 1 H, J=9 Hz), 7.71 (m, 3 H), 7.6 (d, 1 H, J=8.1 Hz), 7.44 (m, 2 H), 6.25 (s, 1 H), 6.08 (broad s, 1 H).

Intermediate 3

6-Bromo-4-(3,4-dichlorophenyl)amino-2-hydroxyquinoline

Prepared using general procedure 1; 6-Bromo-2,4-quinolinediol (3 g, 12.5 mmol), 3,4-dichloroaniline, 6.25 mL of 2 M HCl in Et$_2$O were irradiated to 180° C. (400 W max) for 40 min. to afford 1.94 g (5.05 mmol, 40%). $^1$H NMR (300 MHz, DMSO): 11.36 (s, 1H), 8.83(s, 1H), 8.28(s, 1H), 7.70(dd, 1H, J=8.88, 1.61 Hz), 7.64(d, 1H, J=8.88 Hz), 7.55(d, 1H, J=2.02 Hz), 7.33(dd, 1H, J=8.88, 2.42 Hz), 7.25(d, 1H, J=8.88 Hz), 5.86(s, 1H).

Intermediate 4

6-Fluoro-4-(3,4-dichlorophenyl)amino-2-hydroxyquinoline

Prepared using general procedure 1; 6-Fluoro-2,4-dichloroquinolinediol (2.5 g, 13.95 mmol), 3,4-dichloroaniline (4.5 g, 27.91 mmol), 5 mL of 4 M HCl in dioxane (20 mmol) were irradiated to 180° C. (400 W max) for 40 min. Pouring onto methanol followed by collection of the solids, afforded 2.136 g of material (6.61 mmol, 47%). $^1$H NMR (300 MHz, DMSO): 11.48(s, 2H), 8.74(s, 1H), 7.92(dd, 1H, J=10.70, 2.60 Hz), 7.65(d, 1H, J=8.88 Hz), 7.56(d, 1H, J=2.42 Hz), 7.49(d, 1H), 7.33(m, 2H), 5.89(s, 1H).

Intermediate 5

8-Bromo-2-Hydroxy-4-(2,3-dichlorophenyl)aminoquinoline

Prepared using general procedure 1; 8-Bromo-2,4-quinolinediol (4 g, 16.66 mmol), 3,4-dichloroaniline (8 g, 49.38 mmol), 2.78 mL of 6 M HCl (16.68 mmol) and 20 mL NMP were irradiated to achieve 200° C. (400 W max) for 30 min. Cooling and precipitation by pouring onto 100 mL water afforded 3.52 g of product (9.16 mmol, 55%). $^1$H NMR (300 MHz, DMSO): 9.77(s, 2H), 8.95(s, 1H), 8.11(dd, 1H, J=8.48, 0.81 Hz), 7.89(dd, 1H, J=7.67, 0.81 Hz), 7.66(d, 1H, J=8.88 Hz), 7.58(d, 1H, J=2.42 Hz), 7.36(dd, 2H, J=8.48, 2.42 Hz), 7.20(t, 1H, J=8.07 Hz), 5.88(s, 1H).

Intermediate 6

8-Fluoro-2-Hydroxy-4-(2,3-dichlorophenyl)aminoquinoline

Prepared using general procedure 1; 8-Bromo-2,4-quinolinediol (4 g, 22.33 mmol), 3,4-dichloroaniline (10.88 g, 66.66 mmol), 3.7 mL of 6 M HCl (22.2 mmol) and 20 mL NMP were irradiated to achieve 200° C. (400 W max) for 30 min. Cooling and precipitation by pouring onto 100 mL water afforded 3.2 g of product (9.90 mmol, 44%). $^1$H NMR (300 MHz, DMSO): 9.80(s, 2H), 8.94(s, 1H), 8.12(d, 1H, J=8.48 Hz), 7.90(d, 1H, J=7.67 Hz), 7.66(d, 1H, J=8.88 Hz), 7.58(d, 1H, J=2.42 Hz), 7.37(dd, 1H, J=8.88, 2.42 Hz), 7.12(t, ?H, J=7.87 Hz), 5.90(s, 1H).

Intermediate 7

8-Bromo-2-chloro-4-(3,4-dichlorophenyl)aminoquinoline

General Procedure 3

8-Bromo-2-hydroxy-4-(3,4-dichlorophenyl)aminoquinoline (3.52 g, 9.16 mmol) and 26 mL of POCl$_3$ were heated to 120° C. for 4 h. The bulk of the POCl$_3$ was distilled (~18 mL), and the reaction cooled. The solution was poured slowly onto warm water to get a gummy solid. The water was decanted and the solids washed with several portions of water. A final wash with toluene and drying under vacuum afforded 1.43 g of material (3.55 mmol, 38.8%). $^1$H NMR (300 MHz, DMSO): 9.58(s, 1H), 8.39(d, 1H, J=8.48 Hz), 8.15(d, 1H, J=7.67 Hz), 7.70(d, 1H, J=8.88 Hz), 7.66(d, 1H, J=2.42 Hz), 7.51(dd, 1H, J=8.48, 7.67 Hz), 7.44(d, 1H, J=8.88, 2.42 Hz), 6.90(s, 1H).

Intermediate 8

8-Fluoro-2-chloro-4-(3,4-dichlorophenyl)aminoquinoline

Prepared using general procedure 3; 8-Fluoro-2-hydroxy-4-(3,4-dichlorophenyl)aminoquinoline (3.2 g, 9.90 mmol) and 23 mL of $POCl_3$ were heated to 120° C. for 4 h. Isolation afforded 0.69 g of material (1.98 mmol, 20%). $^1$H NMR (300 MHz, DMSO): 9.50(s, 1H), 8.17(d, ?H, J=7.67 Hz), 8.04(d, 1H, J=5.25 Hz), 7.79(d, 1H, J=5.65 Hz), 7.71(d, 1H, J=8.88 Hz), 7.61(m, 1H), 7.45(dd, 1H, J=8.88, 2.42 Hz), 6.88(s, 1H).

Intermediate 9

2-Chloro4-(3,4-dichlorophenyl)aminoquinoline

Prepared using general procedure 3; 2-Hydroxy-4-(3,4-dichlorophenyl)aminoquinoline (1.5 g, 4.9 mmol) and 9.2 mL of $POCl_3$ were heated to 120° C. for 4 h. Isolation afforded 1.075 g of material (3.32 mmol, 68%). $^1$H NMR (300 MHz, DMSO): 9.61(s, 1H), 8.40(d, 1H, J=8.07 Hz), 7.82(m, 2H), 7.65(m, 3H), 7.45(dd, 1H, J=8.68, 2.63 Hz), 6.87(s, 1H).

Intermediate 10

6-Bromo-2-chloro-4-(3,4-dichlorophenyl)aminoquinoline

Prepared using general procedure 3; 6-Bromo-2-hydroxy-4-(3,4-dichlorophenyl)aminoquinoline (1.94 g, 5.05 mmol) and 30 mL of $POCl_3$ were heated to 120° C. for 4 h. Isolation afforded 1.209 g of material (3.00 mmol, 60%). $^1$H NMR (300 MHz, DMSO): 9.69(s, 1H), 8.71(s, 1H), 7.91(d, 1H, J=8.88 Hz), 7.78(d, 1H, J=8.88 Hz), 7.69(d, 1H, J=8.88 Hz), 7.68(s, 1H), 7.44(dd, 1H, J=8.68, 2.22 Hz), 6.91(m, 1H).

Intermediate 11

6-Fluoro-2-chloro-4-(3,4-dichlorophenyl)aminoquinoline

Prepared using general procedure 3; 6-Fluoro-2-hydroxy-4-(3,4-dichlorophenyl)aminoquinoline (2.136 g, 6.6 mmol) and 30 mL of $POCl_3$ were heated to 120° C. for 4 h. Isolation afforded 0.654 g of material (1.914 mmol, 29%). $^1$H NMR (300 MHz, DMSO): 9.55(s, 1H), 8.27(dd, 1H, J=10.50, 2.02 Hz), 7.92(dd, 1H, J=8.88, 5.65 Hz), 7.70(m, 3H), 7.45(dd, 1H, J=8.48, 2.02 Hz), 6.90(s, 1H).

Intermediate 12

6-Methoxy-2-chloro-4-(3,4-dichlorophenyl)aminoquinoline

Prepared using general procedure 3; 6-Methoxy-2-hydroxy-4-(3,4-dichlorophenyl)aminoquinoline (1.05 g, 3.13 mmol) and 26 mL of $POCl_3$ were heated to 120° C. for 4 h. Isolation afforded 0.685 g of material (1.94 mmol, 61%).

Intermediate 13

4-Chloro-2-(N-2-(4-morpholino)phenylamino)quinoline 2,4-Dichloroquinoline (300 mg, 1.51 mmol), 2-morpholinoaniline (297 mg, 1.66 mmol), 1 M HCl in $Et_2O$ (3 mL) and NMP (3 mL) were added to a 10 mL Schlenk Flask. The ether was removed with a stream of nitrogen, and the flask heated to 130° C. for 16 h. The reaction was cooled and passed through a 500 mg tC18 Sep Pak© (Waters Corp), and purified on 3×100 Novapak HR RCM segments using methanol/water/0.1% TFA at 25 mL per min. Evaporation of the solvents afforded 326.2 mg of product as a TFA salt (0.718 mmol, 48%) along with the product arising from bis-addition (116 mg, 0.22 mmol, 15%). Bis-addition $^1$H NMR (DMSO, 300 mHz): 12.31(s, 1H), 9.90(s, 1H), 9.70(s, 1H), 8.49 (d, 1H, J=8.48 Hz), 7.84 (m, 2H), 7.57 (m, 1H), 7.33 (m, 4H), 7.14 (m, 4H), 5.85 (s, 1H), 3.38(s, 8H), 2.87 (s, 4H).

Intermediate 14

4-(2-methoxyethylamino)-2-hydroxyquinoline

Prepared as in general procedure 1; Quinoline diol (1 g, 6.2 mmol), 2-methoxyethylamine (700 mg, 9.3 mmol) afforded 722 mg of product (53%) which was taken on directly.

Intermediate 15

2-Chloro-4-(2-methoxyethylamino)quinoline

Prepared using general procedure 3; 4-(2-methoxyethylamino)-2-hydroxyquinoline (611 mg, 2.8 mmol) and 2.5 mL of $POCl_3$ were heated to 120° C. for 8 days. Isolation afforded 610 mg of material (92%).

Diversification Library: General Procedure 4

2-Chloroquinoline intermediates (prepared above) (300 mg) were coupled with 2 equivalents of amine (from Table I) using a ChemSpeed robot. Each coupling was carried out in NMP for the time and temperature indicated in Table 2, and the isolated yield was calculated for >50% of the entries. The compounds were characterized with HPLC, HPLC-MS and purified by preparative HPLC.

TABLE 1

Amine reagents used in synthesis of compounds of the present invention.

| A | 2-hydroxyaniline | B | 2-methoxyaniline |
|---|---|---|---|
| C | 2-methylaniline | D | 2-aminoaniline |
| E | 2-fluoroaniline | F | Aniline |
| G | 3,4-dichloroaniline | H | 4-fluoro-3-chloroaniline |
| J | 3,4-dimethoxyamine | L | 2-morpholinoaniline |
| M | 6-aminobenzothiazole | N | 4-fluoroaniline |
| O | 2-chloroaniline | | |

EXAMPLES

Exemplary compounds 1 to 34 inclusive are illustrated in Table 2 which shows the name of each compound and the specifics of reaction time, reaction temperature, yield and molecular ion. Quinoline precursors were prepared by the general procedures 1, 2 and 3 as appropriate, reacted with an amine from Table 1 as indicated, using general procedure 4.

TABLE 2

Physical data for Examples 1–34.

| Ex. # | amine | Compound Name | yield | time | temp. | MS (m + H) |
|---|---|---|---|---|---|---|
| 1 | L | N2,N4-bis-(2-morpholin-4-yl-phenyl)-quinoline-2,4-diamine | 29 | 17:00 | 130 | 482 |
| 2 | L | N4-(3,4-Dichloro-phenyl)-N2-(2-morpholin-4-yl-phenyl)-quinoline-2,4-diamine | 74 | 24:00 | 107 | 465 |
| 3 | B | 8-Bromo-N4-(3,4-dichloro-phenyl)-N2-(2-methoxy-phenyl)-quinoline-2,4-diamine | 45 | 16:00 | 180 | 488 |
| 4 | C | 8-Bromo-N4-(3,4-dichloro-phenyl)-N2-o-tolyl-quinoline-2,4-diamine | 36 | 16:00 | 180 | 472 |
| 5 | E | 8-Bromo-N4-(3,4-dichloro-phenyl)-N2-(2-fluoro-phenyl)-quinoline-2,4-diamine | 76 | 16:00 | 180 | 476 |
| 6 | O | 8-Bromo-N2-(2-chloro-phenyl)-N4-(3,4-dichloro-phenyl)-quinoline-2,4-diamine | 58 | 16:00 | 180 | 492 |
| 7 | A | 2-[8-Bromo-4-(3,4-dichloro-phenylamino)-quinolin-2-ylamino]-phenol | 46 | 16:00 | 180 | 474 |
| 8 | D | N2-(2-Amino-phenyl)-8-bromo-N4-(3,4-dichloro-phenyl)-quinoline-2,4-diamine | 34 | 16:00 | 180 | 473 |
| 9 | A | 2-[4-(3,4-Dichloro-phenylamino)-quinolin-2-ylamino]-phenol | 56 | 18:00 | 150 | 396 |
| 10 | B | N4-(3,4-Dichloro-phenyl)-N2-(2-methoxy-phenyl)-quinoline-2,4-diamine | 54 | 18:00 | 150 | 410 |
| 11 | C | N4-(3,4-Dichloro-phenyl)-N2-o-tolyl-quinoline-2,4-diamine | 59 | 18:00 | 150 | 394 |
| 12 | A | 2-[4-(3,4-Dichloro-phenylamino)-8-fluoro-quinolin-2-ylamino]-phenol | 54 | 16:00 | 180 | 414 |
| 13 | B | N4-(3,4-Dichloro-phenyl)-8-fluoro-N2-(2-methoxy-phenyl)-quinoline-2,4-diamine | 36 | 16:00 | 180 | 428 |
| 14 | D | N2-(2-Amino-phenyl)-N4-(3,4-dichloro-phenyl)-8-fluoro-quinoline-2,4-diamine | 54 | 16:00 | 180 | 413 |
| 15 | F | N4-(3,4-Dichloro-phenyl)-8-fluoro-N2-phenyl-quinoline-2,4-diamine | 32 | 16:00 | 180 | 398 |
| 16 | E | N4-(3,4-Dichloro-phenyl)-8-fluoro-N2-(2-fluoro-phenyl)-quinoline-2,4-diamine | 22 | 16:00 | 180 | 416 |
| 17 | C | 6-bromo-N4-(3,4-dichloro-phenyl)-N2-o-tolyl-quinoline-2,4-diamine | 57 | 16:00 | 150 | 472 |
| 18 | D | N2-(2-amino-phenyl)-6-bromo-N4-(3,4-dichloro-phenyl)-quinoline-2,4-diamine | 65 | 16:00 | 150 | 473 |
| 19 | E | 6-bromo-N4-(3,4-dichloro-phenyl)-N2-(2-fluoro-phenyl)-quinoline-2,4-diamine | 67 | 16:00 | 150 | 476 |
| 20 | F | 6-bromo-N4-(3,4-dichloro-phenyl)-N2-phenyl-quinoline-2,4-diamine | 89 | 16:00 | 150 | 458 |
| 21 | A | 2-[4-(3,4-dichloro-phenylamino)-6-fluoro-quinolin-2-ylamino]-phenol | 65 | 16:00 | 150 | 414 |
| 22 | E | N4-(3,4-dichloro-phenyl)-6-fluoro-N2-(2-fluoro-phenyl)-quinoline-2,4-diamine | 36 | 16:00 | 150 | 416 |
| 23 | F | N4-(3,4-dichloro-phenyl)-6-fluoro-N2-phenyl-quinoline-2,4-diamine | 68 | 16:00 | 150 | 398 |
| 24 | B | N4-(3,4-dichloro-phenyl)-6-methoxy-N2-(2-methoxy-phenyl)-quinoline-2,4-diamine | 12 | 16:00 | 150 | 440 |
| 25 | C | N4-(3,4-dichloro-phenyl)-6-methoxy-N2-o-tolyl-quinoline-2,4-diamine | 30 | 16:00 | 150 | 424 |
| 26 | B | 6-bromo-N4-(3,4-dichloro-phenyl)-N2-(2-methoxy-phenyl)-quinoline-2,4-diamine | 27 | 16:00 | 105 | 488 |
| 27 | D | N2-(2-amino-phenyl)-N4-(3,4-dichloro-phenyl)-quinoline-2,4-diamine | 34 | 16:00 | 150 | 395 |
| 28 | E | N4-(3,4-dichloro-phenyl)-N2-(2-fluoro-phenyl)-quinoline-2,4-diamine | 65 | 16:00 | 150 | 398 |
| 29 | F | N4-(3,4-dichloro-phenyl)-N2-phenyl-quinoline-2,4-diamine | 48 | 16:00 | 150 | 380 |

TABLE 2-continued

Physical data for Examples 1–34.

| Ex. # | amine | Compound Name | yield | time | temp. | MS (m + H) |
|---|---|---|---|---|---|---|
| 30 | A | 2-[6-bromo-4-(3,4-dichloro-phenylamino)-quinolin-2-ylamino]-phenol | 82 | 16:00 | 150 | 474 |
| 31 | F | 8-bromo-N4-(3,4-dichloro-phenyl)-N2-phenyl-quinoline-2,4-diamine | 15 | 16:00 | 180 | 458 |
| 32 | D | N2-(2-amino-phenyl)-N4-(3,4-dichloro-phenyl)-6-methoxy-quinoline-2,4-diamine | 45 | 16:00 | 150 | 425 |
| 33 | E | N4-(3,4-dichloro-phenyl)-N2-(2-fluoro-phenyl)-6-methoxy-quinoline-2,4-diamine | 63 | 16:00 | 150 | 428 |
| 34 | F | N4-(3,4-dichloro-phenyl)-6-methoxy-N2-phenyl-quinoline-2,4-diamine | 35 | 16:00 | 150 | 410 |

Biological data for selected compounds is shown in Table 3.

TABLE 3

Biological Data

| Ex. # | Compound Structure | Formalin test % inhibition (dose, time route) | FLIPr IC$_{50}$ (N) |
|---|---|---|---|
| 2 | 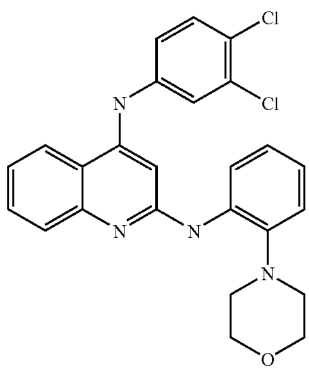 | 42 (60, 40, IP) | 10.00 |
| 14 | 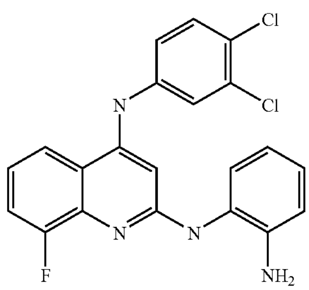 | | 4.01 |
| 27 | 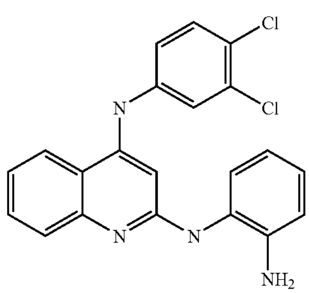 | | 9.82 |

TABLE 3-continued

Biological Data

| Ex. # | Compound Structure | Formalin test % inhibition (dose, time route) | FLIPr IC$_{50}$ (N) |
|---|---|---|---|
| 33 | 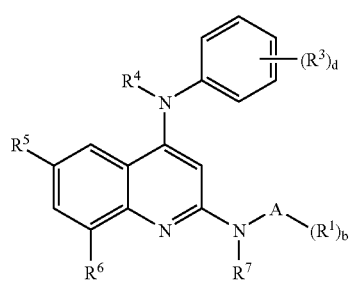 | | 10.00 |

The invention claimed is:

1. A compound of formula I:

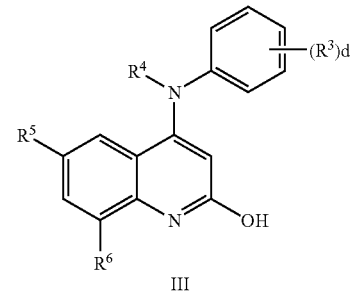

wherein:

A is phenyl or morpholine;

R$^1$ at each occurrence is independently selected from halogen, (C$_1$–C$_6$)alkyl, heterocyclyl, OH, (C$_1$–C$_6$)alkoxy or NR$^2$$_2$;

b is an integer selected from 0, 1, 2 or 3;

R$^2$ at each occurrence is independently selected from H or (C$_1$–C$_4$)alkyl;

R$^3$ at each occurrence is independently selected from halogen or (C$_1$–C$_4$)alkyl;

d is an integer selected from 0, 1, 2 or 3;

R$^4$ is selected from H or (C$_1$–C$_4$)alkyl;

R$^5$ is selected from the group consisting of H, halogen, (C$_1$–C$_3$)alkyl, (C$_1$–C$_3$)perfluoroalkyl, (C$_1$–C$_3$)alkoxy, hydroxy, NH$_2$ or NHR$^2$;

R$^6$ is selected from H, halogen, (C$_1$–C$_6$)alkyl, (C$_1$–C$_4$)perfluoroalkyl, (C$_1$–C$_6$)alkoxy, hydroxy, (C$_1$–C$_6$)alkanoyl, C(=O)NR$^2$$_2$ or —NR$^2$$_2$; and R$^7$ selected from H or methyl.

2. A compound of claim 1 wherein:

R$^4$ and R$^7$ are H; and

R$^5$ is selected from H, halogen, (C$_1$–C$_3$)alkyl, (C$_1$–C$_3$)perfluoroalkyl or (C$_1$–C$_3$)alkoxy.

3. A method for the treatment of pain in a subject suffering therefrom, comprising administering to said subject a pain-ameliorating effective amount of a compound according to claim 1.

4. A pharmaceutical composition comprising a therapeutically-effective amount of a compound according to claim 1 together with at least one pharmaceutically-acceptable excipient or diluent.

5. A method for preparing a compound according to claim 1, said method comprising:

a) reacting a substituted 2,4-quinolinediol (formula II) with three equivalents of an aryl amine in N-methylpyrrolidinone and 6N HCl in 2-propanol, in a sealed tube at a temperature of about 180° C.;

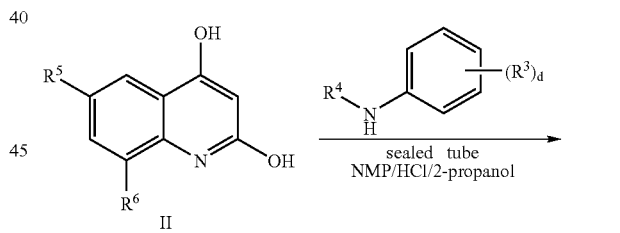

wherein R$^3$, R$^4$, R$^5$, R$^6$ and d are as defined as in claim 1;

b) chlorinating the 2-hydroxy-4-aminoquinoline compound according to formula III by refluxing with POCl$_3$ to form a compound according to formula IV;

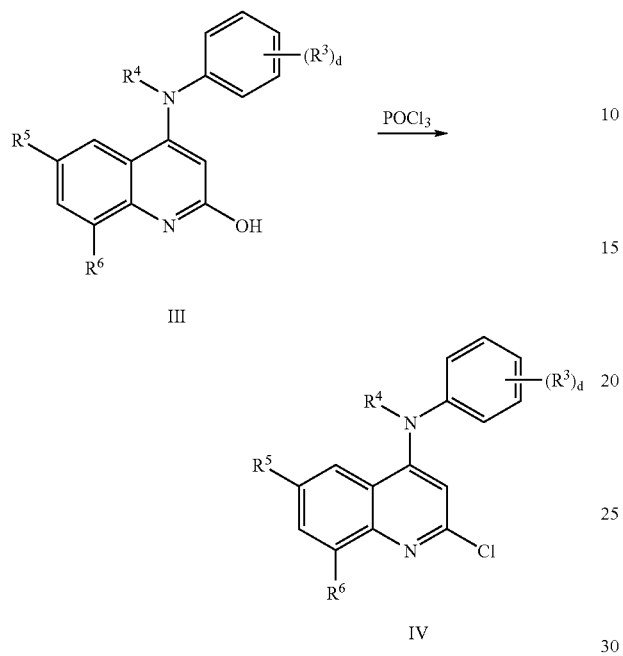

wherein R$^3$, R$^4$, R$^5$, R$^6$ and d are as defined as in claim 1; and c) reacting the 2-chloro-4-aminoquinoline compound with a compound having the formula R$^7$—NH—A—(R$^1$)b in N-methylpyrrolidinone at a temperature of 100–180° C.;

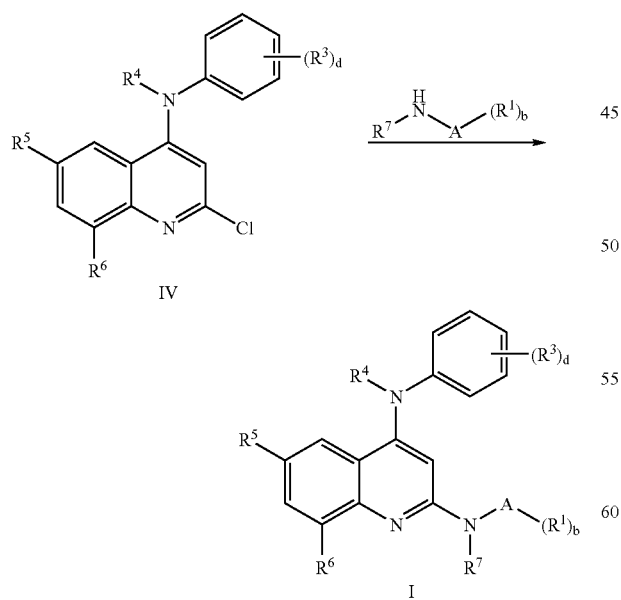

wherein R$^1$, R$^3$, R$^4$, R$^5$, R$^6$, R$^7$, A, b, and d are as defined as in claim 1.

6. The method according to claim 5, wherein step c) is performed in a parallel fashion using robotic instrumentality.

7. A method for preparing a compound according to claim 1, said method comprising:

a) reacting a substituted 2,4-quinolinediol in accord with formula II with two equivalents of an aryl amine in N-methylpyrrolidinone and 4 M HCl in dioxane, in a sealed tube using microwave irradiation at a 400 W upper set point to maintain a 200° C. temperature for 30 minutes;

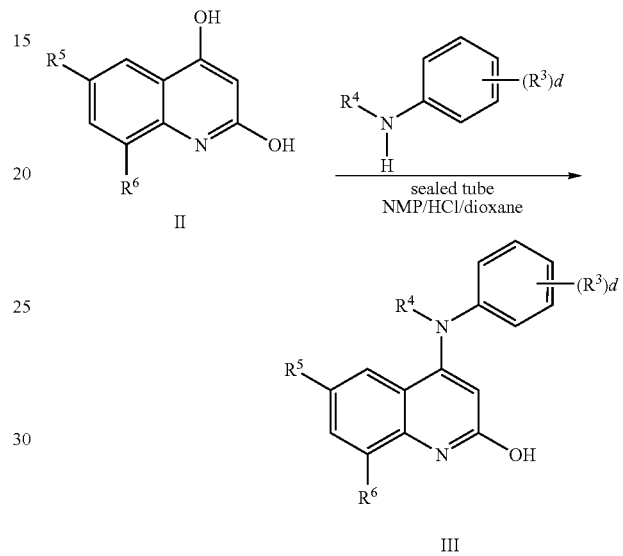

wherein R$^3$, R$^4$, R$^5$, R$^6$ and d are as defined as in claim 1;

b) chlorinating the 2-hydroxy-4-aminoquinoline compound according to formula III by refluxing with POCl$_3$ to form a compound according to formula IV;

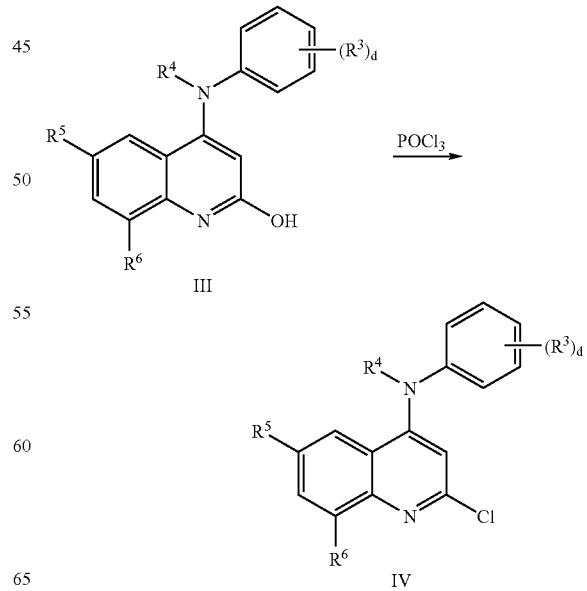

wherein $R^3$, $R^4$, $R^5$, $R^6$ and d are as defined as in claim 1; and c) reacting the 2-chloro-4-aminoquinoline compound with a compound having the formula $R^7$—NH—A—$(R^1)_b$ in N-methylpyrrolidinone at a temperature of 100–180° C.;

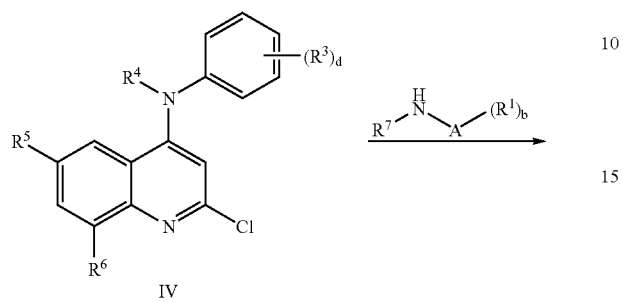

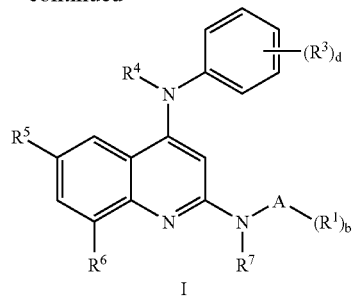

wherein $R^1$, $R^3$, $R^4$, $R^5$, $R^6$, $R^7$, A, b, and d are as defined as in claim 1.

8. The method according to claim 7, wherein step c) is performed in a parallel fashion using robotic instrumentality.

* * * * *